United States Patent [19]

Mogilevsky

[11] 4,100,679
[45] Jul. 18, 1978

[54] DENTAL ARTICULATOR

[76] Inventor: Israel Mogilevsky, 3909 N. 51st Blvd., Milwaukee, Wis. 53216

[21] Appl. No.: 712,496

[22] Filed: Aug. 9, 1976

[51] Int. Cl.² ............................................. A61C 11/00
[52] U.S. Cl. ................................................... 32/32
[58] Field of Search ......................................... 32/32

[56] References Cited

U.S. PATENT DOCUMENTS

| 968,055 | 2/1909 | Howard | 32/32 |
|---|---|---|---|
| 1,096,195 | 5/1914 | Roberts | 32/32 |
| 1,736,006 | 11/1929 | Hagman | 32/32 |
| 1,814,750 | 7/1931 | Fritzenwallner | 32/32 |

FOREIGN PATENT DOCUMENTS

| 1,017,719 | 12/1952 | France | 32/32 |
|---|---|---|---|
| 1,124,255 | 10/1956 | France | 32/32 |

*Primary Examiner*—Russell R. Kinsey
*Assistant Examiner*—John J. Wilson
*Attorney, Agent, or Firm*—Fred Wiviott

[57] ABSTRACT

An articulator for dental models includes upper and lower clamp portions which are pivotally interconnected by a resilient universal hinge joint. Each clamp includes a pivotally mounted first elongate clip member for engaging one side of the respective upper or lower model portions and a second clip member for engaging the opposite side thereof. Resilient means biases the clip members toward each other for resiliently engaging the model portions therebetween. An adjustable stop mounted on the upper and lower clamp portions limits pivotal movement of the model portions toward each other.

10 Claims, 3 Drawing Figures

U.S. Patent   July 18, 1978   4,100,679
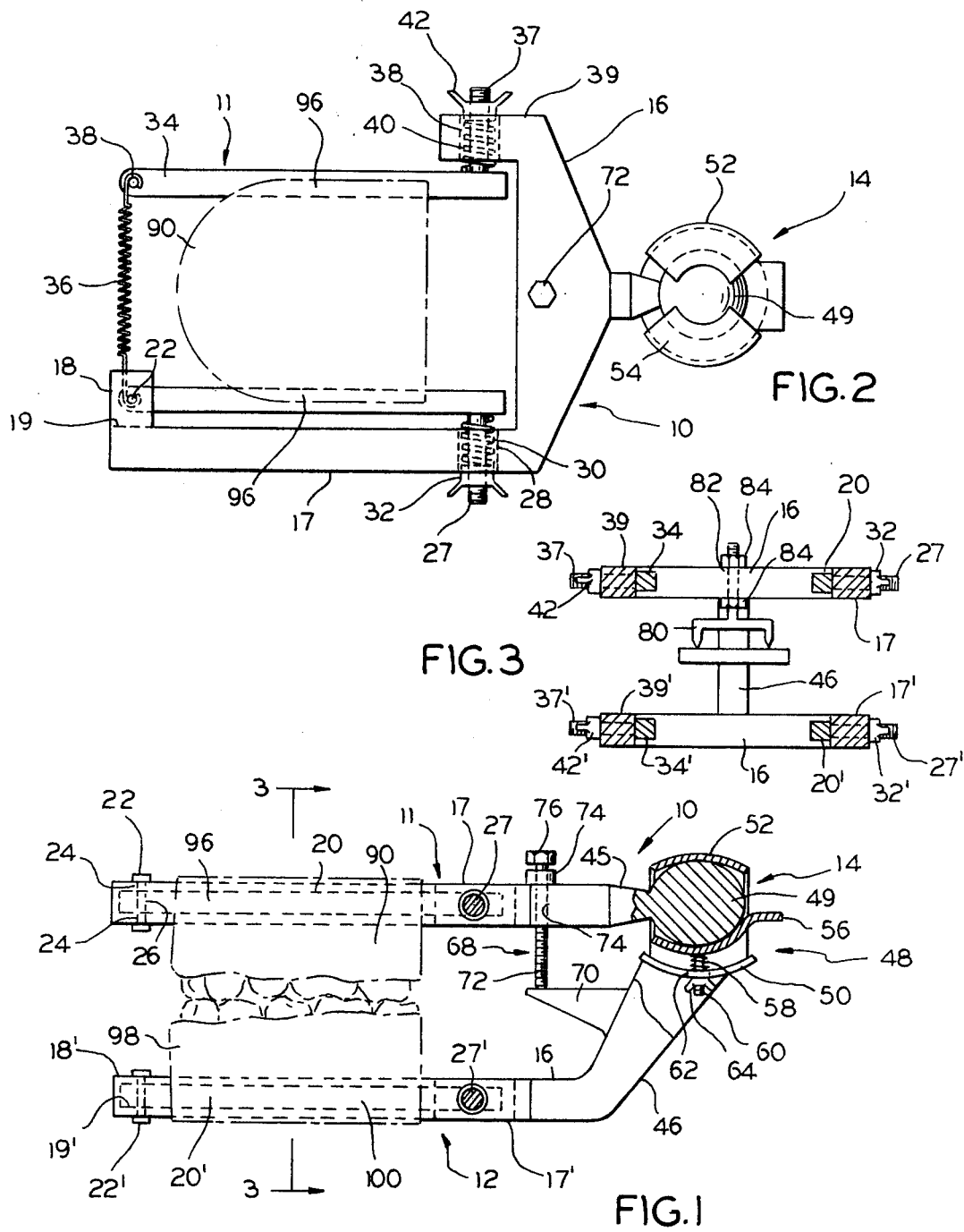

DENTAL ARTICULATOR

BACKGROUND OF THE INVENTION

This invention relates to dental articulators.

It is common practice in the manufacture of dental crowns, caps, partials, bridges and the like to fabricate models of the patient's upper and lower teeth, gums and adjacent jaw portions. The models assist the technician in fitting the denture with the patient's other teeth. Such models are commonly mounted on articulators which comprise an upper and lower support for the upper and lower models, respectively, and which are hingedly connected to simulate the patient's jaw movement. With most prior art articulators, it is necessary to mount the upper and lower models to their associated support portions by means of a plaster or like material. This is a relatively time consuming procedure and limits flexibility. Other prior art articulators which do not require plaster mounting are relatively expensive and complicated.

SUMMARY OF THE INVENTION

It is an object of the invention to provide a new and improved dental articulator.

A further object of the invention is to provide a dental articulator which does not require plaster for attaching the model portions to the upper and lower supports.

A further object of the invention is to provide a dental articulator with a resilient universal hinge joint which simulates jaw movement.

Yet another object of the invention is to provide a relatively simple and economical dental articulator.

A still further object of the invention is to provide a dental articulator which will accommodate various sized models.

These and other objects and advantages of the present invention will become more apparent from the detailed description thereof taken with the accompanying drawings.

BRIEF DESCRIPTION OF THE DRAWINGS

FIG. 1 is a side elevational view, with parts broken away, of the dental articulator according to the invention;

FIG. 2 is a top plan view of the dental articulator illustrated in FIG. 1; and

FIG. 3 illustrates an alternate form of a stop for the articulator shown in FIGS. 1 and 2.

DETAILED DESCRIPTION OF THE PREFERRED EMBODIMENT

Articulator 10 includes an upper frame 11 and a lower frame 12 which are pivotally connected by a resilient hinge joint 14. Upper frame 11 is generally L-shaped in plan view as shown in FIG. 2 and has a base portion 16 and a leg portion 17 extending generally normally to base portion 16. Extending inwardly from the upper end of leg portion 17 is a pivot tip 18 which is slotted at 19 for receiving one end of an elongate clip 20. More specifically, a pivot pin 22 extends through aligned openings 24 and 26 in the pivot tip 18 and clip 20, respectively, for pivotally supporting clip 20 in slot 19. A pin 27 is affixed to and extends outwardly from the opposite end of clip 20 and into an opening 28 formed in leg 20 and adjacent base portion 16. A spring 30 surrounds pin 27 and is held in position by means of a nut 32 which is received on the threaded end of pin 27 for compressing spring 30 and thereby urging the clip 20 to pivot in a counterclockwise direction as viewed in FIG. 2 and about pin 22.

A second elongate clip 34 is disposed at the opposite side of top frame 11 and in general parallelism with clip 20. The second clip 34 is resiliently interconnected with the pivot tip 18 by means of a spring 36 which extends between a pin 38 extending through one end of bar 34 and the pin 22. The opposite end of the second side bar 34 has a pin 37 extending therefrom and through an opening 38 in a short leg portion 39 formed at the opposite end of base 16. A spring 40 surrounds pin 37 and is held in position by means of a nut 42 which is received under the threaded end of pin 37. It will be appreciated that the springs 36 and 40 bias the second clip 34 inwardly toward the first clip 20.

The lower clamp 12 is substantially similar to upper clamp 11 and accordingly, the corresponding parts will be identified by the same reference numeral except that they will be distinguished by means of a prime (').

Specifically, the lower clamp 12 includes a leg portion 17' having an inwardly projecting pivot tip 18' which is slotted at 19' so that a first clip 20' may be pivotally connected by means of a pin 22'. The opposite end of first clip 20' is resiliently urged away from leg portion 17' by means of a spring (not shown) which surrounds a pin 27' extending laterally from first side clip 20'. A second clip (now shown) is also mounted to the base 16' of the lower frame 12 and is substantially identical to the second upper clip 34. The lower frame 12 differs from the upper frame 11 in having an upwardly extending neck portion 46 and which has at its upper end the socket portion 48 of pivot joint 14 while upper frame 11 carries the ball portion 49 thereof.

Specifically, the socket joint includes a dished portion 50 mounted at the upper end of neck 46 and from which extend a pair of side socket portions 52 and 54 which are generally arcuate but have a radius of curvature slightly larger than the ball 49. In addition, a cup-shaped resilient member 56 is disposed below ball 49 and is urged into resilient engagement therewith by means of a spring 58 disposed between member 56 and lower socket portion 50. Spring 58 is held in position and may be compressed by means of a threaded pin 60 affixed to member 56 and extending downwardly therefrom through an enlarged opening 62 in lower socket portion 50 and a nut 64 threaded on the lower end of pin 58 and below socket portion 50.

In order to limit pivotal movement of the upper frame 11 relative to the lower frame 12, a stop assembly 68 is provided. The latter includes a fixed stop 70 projecting inwardly from the neck 46 of the lower frame 12 and a screw 72 which is received in a threaded opening 74 formed in the base 16 of upper frame 11. A nut 74 may be disposed between upper frame 11 and the head 76 of screw 72 to hold the latter in its adjusted position.

An alternate form of the adjustable stop is shown in FIG. 3 to include a bifurcated member 80 which is adjusted relative to an opening 82 formed in the base 16 of the upper frame 11 by means of a pair of nuts 84. The lower end of the member 80 engages a relatively wider stop 86 integrally formed on the lower frame 12 (not shown) in FIG. 3.

In operation of the apparatus just described, the upper dental model 90 is positioned between the clips 20 and 34 of the upper frame assembly 11 and toward this end the nuts 32 and 42 may first be loosened. In addition, in order to facilitate the clamping action between the clips 20 and 34 and the model 90, the latter may be provided with a pair of parallel slots 96 one of which is formed along each side and which are slightly larger in depth and width than the clips 20 and 34. After the clips 20 and 34 have been positioned in the grooves 96, the nuts 32 and 42 are tightened until the upper model 90 is resiliently clamped by clips 20 and 34. The lower model 98 is similarly provided with side slots 100 and is mounted between the lower clips in the same manner as the upper model 90. It will be appreciated that the resilient pivot joint 14 not only permits pivotal movement of the upper frame assembly 11 relative to the lower frame assembly 12 but in addition, some lateral and longitudinal movement to approximate relative movement in the human jaw.

While only a single embodiment of the invention has been illustrated and described, it is not intended to be limited thereby but only by the scope of the appended claims.

I claim:

1. An articulator for dental models including upper and lower clamp portions, first pivot means interconnecting said clamp portions, each of said upper and lower clamp portions including a frame portion and a pair of elongated clip members extending generally away from said first pivot means and each having a remote end and a relatively proximate end with respect to said first pivot means, first resilient means connecting the remote end of one clip member of each pair to the remote end of the other clip member thereof for urging one clip member of each pair of clip members toward the other, the remote end of the other clip member of each pair being pivotally mounted by second and third pivot means on its associated frame portion and at the end thereof remote from said first pivot means and additional resilient means associated with each clamp portion for urging the proximate ends of said clip members inwardly, whereby a dental model may be resiliently clamped between said clip members.

2. The dental articulator set forth in claim 1 wherein each of said upper and lower frame portions include a base and an elongated leg extending from said base and away from said first pivot means, the remote end of said other clip members being pivotally mounted by second and third pivot means to the remote end of its associated leg portion, and said second resilient means comprising spring means effectively engaging said leg portion and said proximate end of said other clip member, said third resilient means comprising spring means effectively engaging said base portion and said proximate end of said one clip member.

3. The dental articulator set forth in claim 2 and including adjustable stop means for limiting the degree of pivotal movement of said upper and lower frame portions toward each other.

4. The dental articulator set forth in claim 3 wherein said pivot first means includes a ball portion formed on one of said frame portions and a socket portion mounted on the other one thereof.

5. The dental articulator set forth in claim 4 wherein said socket portion includes resilient means which yieldingly engages said ball portion for resiliently clamping the same.

6. The dental articulator set forth in claim 5 wherein said socket means includes ball engaging means having a radius of curvature larger than that of said ball means to permit slight lateral and longitudinal movement of said one frame portion relative to the other.

7. The dental articulator set forth in claim 1 wherein said first pivot means includes a ball portion formed on one of said frame portions and a socket portion mounted on the other one thereof.

8. The dental articulator set forth in claim 7 wherein said socket portion includes resilient means which yieldingly engages said ball portion for resiliently clamping the same.

9. The dental articulator set forth in claim 8 wherein said socket means includes ball engaging means having a radius of curvature larger than that of said ball means to permit slight lateral and longitudinal movement of said one frame portion relative to the other.

10. The articulator set forth in claim 1 wherein said additional resilient means comprises second and third resilient means.

* * * * *